(12) United States Patent
Bonrath et al.

(10) Patent No.: US 7,435,836 B2
(45) Date of Patent: Oct. 14, 2008

(54) PROCESS FOR THE MANUFACTURE OF TOCOPHERYL ACYLATES

(75) Inventors: Werner Bonrath, Freiburg (DE); Lisa Giraudi Bijasson, Huningue (FR)

(73) Assignee: DSM IP Assets B.V., TE Heerlen (NL)

( * ) Notice: Subject to any disclaimer, the term of this patent is extended or adjusted under 35 U.S.C. 154(b) by 8 days.

(21) Appl. No.: 11/578,549

(22) PCT Filed: Apr. 18, 2005

(86) PCT No.: PCT/EP2005/004068

§ 371 (c)(1),
(2), (4) Date: Oct. 16, 2006

(87) PCT Pub. No.: WO2005/103026

PCT Pub. Date: Nov. 3, 2005

(65) Prior Publication Data

US 2007/0225509 A1      Sep. 27, 2007

(30) Foreign Application Priority Data

Apr. 26, 2004   (EP) .................................. 04009816

(51) Int. Cl.
*C07D 311/72* (2006.01)

(52) U.S. Cl. ..................................................... 549/410
(58) Field of Classification Search ................. 549/412, 549/410

See application file for complete search history.

(56) References Cited

U.S. PATENT DOCUMENTS 6,239,294 B1    5/2001   Krill et al.
2004/0014996 A1 *  1/2004   Oost et al. ................... 549/410

FOREIGN PATENT DOCUMENTS

DE         196 03 142 A1    7/1997
EP         0 603 695 A1     6/1994
WO         WO 02/42286 A1 *  5/2002

OTHER PUBLICATIONS

Database XP002336034 & JP 49 055633 A, May 30, 1974.

* cited by examiner

*Primary Examiner*—Bernard Dentz
*Assistant Examiner*—David E Gallis
(74) *Attorney, Agent, or Firm*—Nixon & Vanderhye P.C.

(57) ABSTRACT

The present invention relates to a process for the manufacture of a tocopheryl acylate which comprises reacting a tocopherol with an acylating agent in the presence of a solid basic catalyst comprising, an alkali metal and/or alkaline earth metal preferably on a solid carrier and to the use of such catalysts in the acylation of tocopherols.

17 Claims, No Drawings

PROCESS FOR THE MANUFACTURE OF TOCOPHERYL ACYLATES

This application is the US national phase of international application PCT/EP2005/004068 filed 18 Apr. 2005 which designated the U.S. and claims benefit of EP 04009816.2, dated 26 Apr. 2004, the entire content of which is hereby incorporated by reference.

The present invention is concerned with a novel process for the acylation of tocopherols and the use of specific catalysts therein.

The term "tocopherol" as used herein is to be understood to refer to any compound derived from the basic structure of tocol [2-methyl-2-(4',8',12'-trimethyltridecyl)-6-chromanol], having a free 6-hydroxy group and exhibiting vitamin E activity, viz. any tocopherol having the saturated side chain 4',8',12'-trimethyltridecyl, such as $\alpha$-, $\beta$-, $\gamma$-, $\delta$-, $\zeta_2$- or $\eta$-tocopherol, and also any tocotrienol having three double bonds in the side chain [4',8',12'-trimethyltridec-3',7',11'-trienyl], such as $\epsilon$- or $\zeta_1$-tocopherol. Of these various tocopherols (all-rac)-$\alpha$-tocopherol, generally referred to as vitamin E, is of primary interest, being the most active and industrially most important member of the vitamin E group.

The present invention is preferably concerned with a novel process for the manufacture of acylates of tocopherols (tocopheryl acylates), more particularly of tocopheryl acetates. In a more preferred aspect, the present invention is concerned with a process for the manufacture of (all-rac)-$\alpha$-tocopheryl acetate, since this is the main commercial form of vitamin E. $\alpha$-Tocopherol itself and the other tocopherols such as those mentioned above can be readily acylated by the process of the present invention. In general, each of the tocopherols can be acylated in the form of its racemate or of any individual stereoisomer.

The synthesis of $\alpha$-tocopheryl acetate by esterification of $\alpha$-tocopherol with excess acetic anhydride in the absence of a catalyst is described and exemplified by J. D. Surmatis et al. in U.S. Pat. No. 2,723,278. The product (dl)-$\alpha$-tocopherol acetate was formed under reflux conditions for 5 hours; the yield is not given. This reaction can also be carried out with pyridine as the catalyst to afford, after three days reaction at room temperature, $\alpha$-tocopheryl acetate in 96% yield, as reported by N. Cohen et al. on page 1172 of Helv. Chim. Acta 64, 1158-1172(1981). S. Paul et al. (Tetrahedron Letters 43, 4261-4265 [2002]) reported favorable results obtained in the acetylation of hydroxy, thiol and amino compounds using acetic anhydride/pyridine over basic alumina under microwave irradiation for a few until 16 minutes.

Excellent reviews on types of heterogenous basic catalysts and on the catalysis of different reactions by solid basic catalysts have been published by H. Hattori (e.g. in Chem. Rev. 95, 527[1995]) and Y. Ono and T. Baba (Catalysis Today 38, 321-337 [1997]). The use of different bases as catalysts in a diversity of reactions has been reviewed, e.g., by E. J. Doskocil et al. in Catalysis 15, 40-72 [2000], especially their use in double bond isomerization, hydrogenations, aminations, dehydrocyclodimerizations, aldol additions, nitroaldol reactions, Michael additions, conjugate additions of alcohol, cyanoethylation and Tiskchenko reaction.

None of these reviews make reference to the use of solid base catalysts in the acylation of tocopherols.

The novel process according to the present invention provides excellent yields, avoids corrosion problems, can be carried out in the absence of an additional solvent, thus avoiding the need to recycle solvents, and can be carried out in a continuous or batchwise mode.

According to the present invention there is provided a process for the manufacture of an acylate of a tocol (e.g., tocotrienyl acylate or a tocopheryl acylate) which comprises reacting a tocopherol with an acylating agent in the presence of a solid basic catalyst comprising an alkali metal and/or alkaline earth metal, preferably on a solid carrier.

The acylation can be carried out in principle using any acylating agent conventionally used for the acylation of a phenolic hydroxyl group as is present in tocopherols. Especially suitable types of such acylating agents are acid anhydrides and acyl halides. The acyl groups in such acylating agent may be derived from aliphatic carboxylic acids, e.g. from linear or branched chain alkanoic acids, in particular $C_{1-7}$-alkanoic acids such as acetic acid, propionic acid, butyric acid and pivalic acid, or from higher alkanoic acids (fatty acids) with up to 20 carbon atoms such as palmitic acid; or from aromatic carboxylic acids, particularly benzoic acid, so that in each case the appropriate acylate, being an alkanoate, or e.g. the benzoate, respectively, of tocol or the tocopherol is produced in the acylation process. Examples of aliphatic acyl halides are linear or branched chain alkanoyl chlorides such as acetyl, propionyl and butyryl chloride, and, of aromatic acyl halides, benzoyl chloride. The preferred acylating agent is acetic anhydride or acetyl chloride, most preferably acetic anhydride.

The acylation in accordance with the process of the present invention may by carried out in the presence or in the absence of an added solvent, but preferably one of the reactants, i.e. the tocol or tocopherol or the acylating agent, is used in excess and no added solvent used. Preferably, the acylating agent is used in excess, preferably in a one- to about a threefold molar amount, more preferably in a 1.5- to 2.5-fold molar amount, and most preferably in a 1.75- to 2.25-fold molar amount, relative to the molar amount of tocol or tocopherol present in the initial reaction mixture. If an additional solvent is used, however, this is suitably a polar or non-polar aprotic organic solvent, particularly an aliphatic, preferably $C_4$ to $C_{10}$ aliphatic, hydrocarbon, e.g. pentane, hexane, heptane or decane; an alicyclic, preferably $C_4$ to $C_7$ alicyclic, hydrocarbon, e.g. cyclohexane; or an aromatic, particularly $C_6$ to $C_{10}$ aromatic, hydrocarbon, e.g. benzene, toluene, an xylene or naphthalene.

The following types of basic catalysts can be used in the reaction of the present invention:

alkali and alkaline metals; alkali metal oxides and alkaline earth metal oxides; alkali and alkaline earth metal oxides on solid supports; alkali metal amides and fluorides; zeolithes (alkali ion-exchanged and alkali ion-added zeolithes) and clay minerals (hydrotalcites, chrysotiles and sepiolites). For more details see, e.g., Doskocil et al. and Hattori, mentioned above.

Examples of alkali metals used in the solid catalysts of the present invention are Na, K, Rb and Cs, examples of alkaline earth metals are Mg, Ca, Sr and Ba. One or several alkali and/or alkaline earth metals in combination with each other in different weight ratios (since they are not critical) can be used. In a preferred embodiment at least one alkali metal and at least one alkaline earth metal is used, e.g., Na+Ca. The weight ratios of metal: carrier material are not critical either and can vary within wide ranges. They can be, e.g. in the range of 0.1-70% and are preferably in the range of 1-10% if one metal is used and 30-60% if more than one metal is used. All normally useful carriers can be used as support for the metals, such as activated carbon, silica gel, diatomite, alumina, talc, silicates and kaolin with $SiO_2$, $Al_2O_3$ and $TiO_2$ being preferred.

The catalysts are commercially available. Alternatively, they can be prepared as described in the literature or in analogy to methods well-known in the art, e.g., as described by Ono, Y. and Baba, T. in Catalysis Today 38, 321-337 (1997) and in references cited therein, which article is incorporated herein by reference. Catalysts 1-19 and 20-25 (Tables 1 and 2, below) have been prepared and provided by Degussa A G, Hanau, Germany.

Typically, the catalyst is prepared from an aqueous solution of an alkali or alkaline earth metal salt, such as a hydroxide, carbonate, nitrate, chloride, acetate or silicate. The solid carrier is doped with the metal salt in a manner known per se, e.g., by impregnation, soaking or ion-exchange. The wet material is then dried and calcined at a temperature in the range of 150° C. and 800° C., preferably 200° C.-700° C. and most preferably 300° C.-650° C. The desired final concentration of the metal ions in the catalyst is achieved empirically by using correspondingly concentrated aqueous solutions. Catalysts can also be prepared by mixing or moulding the solid components with each other with or without addition of solvents.

In a preferred embodiment of the invention the solid base catalyst is added to the reaction mixture in pure solid form without further activation or modification. The amount of catalyst used is based on the amount of the reactant, i.e. the tocopherol or the acylating agent, usually the former, which is used in the lesser molar amount and is suitably in the range from about 0.005 to about 15 mmol, preferably from about 0.01 to about 1.0 mmol, based on said lesser molar amount, when the process is effected in a batchwise operational mode per 38.4 mmol tocol. For the alternative continuous operational mode, the relative amount of catalyst will have to be adjusted to the size of the reactor and the flow of the reactants. In this case it will be appreciated that the determination of the appropriate relative amount based on the figures for the batchwise operational mode is within the normal skill of the production chemist.

The acylation process in accordance with the present invention is conveniently carried out at temperatures from about 80° C. to about 120° C., preferably from about 90° C. to about 110° C.

Moreover, the process is conveniently carried out under an inert gas atmosphere, preferably under gaseous nitrogen or argon, especially the former.

The progress of the reaction is suitably monitored by analytical means, such as gas chromatography of samples taken from the reaction mixture at various time intervals during the reaction.

After completion of the acylation the produced tocopheryl acylate can be isolated by distilling off, preferably under reduced pressure, acylating agent, and the secondary product formed in the acylation, e.g., acetic acid when acetic anhydride is used as the acylating agent, followed by further distillation, also preferably under reduced pressure, to collect as pure a fraction of the desired acylation product as required.

The main advantage of the use of the catalysts of the present invention in the acylation of tocopherols is that no epimerization of the chromane center occurs when starting from optically pure tocopherol and that with specific catalysts, e.g., those comprising Na+Ca, reaction time can be reduced considerably.

The acylation process of the present invention is illustrated in more detail by the following Examples.

General

All reactions were carried out under argon. (all-rac)-α-Tocopherol, (2R,4'R,8'R)-α-tocopherol, KF on $Al_2O_3$ (Fluka, No 60244) and acetic anhydride (commercial products) and (all-rac)-γ-tocopherol (laboratory material) were used without further purification. The solid basic catalysts were obtained from Degussa and were used without further activation or modification. They can be prepared as described in Example 1. The crude products were analyzed by GC. The GC-analyses were carried out with a gas chromatograph HP 6890 equipped with an autosampler HP 7673, split-injector, and FID. A capillary column Restek XTI 5 (fused silica) was used (30 m×0.32 mm, film 0.25 μm). The applied temperature program was: 150° C. (0 min)–>5° C./min–>335° C. (8 min). Retention times $t_R$ of (all-rac)-α-tocopherol or (2R,4'R,8'R)-α-tocopherol (detected as silyl derivative)=26.4 min, and $t_R$ (all-rac)-α-tocopheryl acetate or (2R,4'R,8'R)-α-tocopheryl acetate=27.0 min. Retention times $t_R$ of (all-rac)-γ-tocopherol (detected as silyl derivative)=24.5 min, and $t_R$ (RRR)-γ-tocopheryl acetate=26.1 min.

For chiral HPLC analyses, samples were dissolved in 5 ml ethanol and 5 μl of sample was injected onto a Chiralpak OP(+) column (240×4.6 mm, flow 0.5 ml/min). The column was eluted with 5 vol % water in methanol. The retention times were as follows: (2R,4'R,8'R)-α-tocopheryl acetate 13.2 min and (2S,4'R,8'R)-α-tocopheryl acetate 24.5 min.

The following Examples illustrate the present invention in more detail.

EXAMPLE 1

(a) Preparation of catalyst 11 (5% Ca on $Al_2O_3$).

Commercially available $Al_2O_3$, having a pore volume of about 0.7 ml/g (determined by water uptake) and a specific surface of about 250 $m^2$/g, was soaked with an aqueous calcium nitrate solution of appropriate concentration in a manner that the amount of solution matched with the pore volume. The catalyst thus obtained was dried at 120° C. and then calcined for 2 hours at 500° C. under air.

(b) Preparation of catalyst 19 (4% Na, 10% Ca on $Al_2O_3$).

A 10% Ca on $Al_2O_3$ catalyst (obtained in an analogous way as described under (a)) was soaked with an appropriate sodium silicate solution in an analogous way, dried and calcined for 2 hours at 500° C. to yield the catalyst with the desired concentration of sodium and calcium.

EXAMPLE 2

Preparation of (all-rac)-α-tocopheryl acetate.

In a 50-ml four-necked flask equipped with a KPG-stirrer, thermometer, and a reflux condenser with an argon inlet, 16.8 g (38.3 mmol) of (all-rac)-α-tocopherol were dissolved in 8.23 g (80.6 mmol) of acetic anhydride in the presence of 0.5 g catalyst No 21 (5% K on $Al_2O_3$). The mixture was stirred at 380 rpm and heated at 100° C. (internal temperature) for 21 h. The mixture was cooled to 24° C., neutralized with 5 g $Na_2CO_3$, filtered, washed with 70 ml heptane and evaporated under reduced pressure (10 mbar, 40° C.). 18.56 g of a brownish oil was obtained representing α-tocopheryl acetate with a purity of 94.54%, (analyzed by GC, int. standard). Yield 96.9%, based on α-tocopherol. The crude product was further purified by bulb-to-bulb distillation at 210° C. (0.016 mbar). The pure product was isolated as colorless-light yellowish oil in 94.88% purity (GC, int. standard). Yield 16.87 g (all-rac)-α-tocopheryl acetate, 93.2% based on (all-rac)-α-tocopherol. In the distillation residue 1.5% of (all-rac)-α-tocopherol acetate was detected.

EXAMPLE 3

Preparation of (all-rac)-α-tocopheryl acetate.

In a 50-ml four-necked flask equipped with a KPG-stirrer, thermometer, and a reflux condenser with an argon inlet, 16.8 g (38.3 mmol) of (all-rac)-α-tocopherol were dissolved in 8.23 g (80.6 mmol) of acetic anhydride in the presence of 0.5 g catalyst No 25 (5% Mg on $Al_2O_3$). The mixture was stirred at 380 rpm and heated at 100° C. (internal temperature) for 19 h. The mixture was cooled to 25° C., neutralized with 5 g $Na_2CO_3$, filtered, washed with 70 ml heptane and evaporated under reduced pressure (10 mbar, 40° C.). 18.72 g of a brownish oil was obtained representing (all-rac)-α-tocopheryl acetate with a purity of 92.93% (analyzed by GC, int. standard). Yield 96.1%, based on α-tocopherol. The crude product was further purified by bulb-to-bulb distillation at 206° C. (0.007 mbar). The pure product was isolated as colorless-light yellowish oil in 94.33% purity (GC, int. standard). Yield 17.01 g of (all-rac)-α-tocopheryl acetate, 94.0% based on (all-rac)-α-tocopherol. In the distillation residue 0.4% of (all-rac)-α-tocopherol acetate was detected.

The yields of (all-rac)-α-tocopheryl acetate using other solid basic catalysts of the invention are shown in the following Table.

TABLE 1

Reaction of (all-rac)-α-tocopherol with acetic anhydride

| Catalyst | Metal content | Carrier | (all-rac)-α-Tocopheryl acetate Yield (%)* | Yield (%)** | α-Tocopherol Yield (%)* |
|---|---|---|---|---|---|
| 1(*) | 11% Ca + 50% Na | $SiO_2$ | 98.6 | 95.6 | 0 |
| 2(*) | 22% Ca + 26% Na | $SiO_2$ | 96.7 | 96.2 | 0 |
| 3 | 1% Ca | $SiO_2$ | 97.4 | 95.6 | 0.15 |
| 4 | 5% Ca | $SiO_2$ | 98.0 | 95.6 | 0.33 |
| 5 | 5% Ca | $SiO_2$ | 95.8 | 95.6 | 0.67 |
| 6 | 1% Cs | $SiO_2$ | 95.6 | 92.1 | 2.41 |
| 7 | 5% Cs | $SiO_2$ | 97.0 | 95.2 | 0.08 |
| 8 | 1% K | $SiO_2$ | 95.8 | 94.6 | 0.27 |
| 9 | 0.5% Ca | $Al_2O_3$ | 95.8 | 94.5 | 0.67 |
| 10 | 8% Ca | $Al_2O_3$ | 95.8 | 93.6 | 1.36 |
| 11 | 5% Ca | $Al_2O_3$ | 93.9 | 93.6 | 1.90 |
| 12 | 10% Ca | $Al_2O_3$ | 94.4 | 92.5 | 2.0 |
| 13 | 10% Ca | $Al_2O_3$ | 95.6 | 94.2 | 0 |
| 14 | 10% Ca | $Al_2O_3$ | 95.6 | 94.3 | 0.17 |
| 15 | 1% Ba | $Al_2O_3$ | 95.1 | 92.8 | 1.86 |
| 16 | 5% K | $Al_2O_3$ | 96.5 | 95.5 | 0 |
| 17 | 1% Sr | $Al_2O_3$ | 96.2 | 95.2 | 0.68 |
| 18 | 10% Ca + 2% Na | $Al_2O_3$ | 96.2 | 94.0 | 0 |
| 19 | 10% Ca + 4% Na | $Al_2O_3$ | 98.2 | 95.8 | 0 |
| 20 | 21% K | $Al_2O_3$ | 99.4 | 96.1 | 0 |
| 21 | 5% K | $Al_2O_3$ | 96.9 | 94.7 | 0 |
| 22 | 2% K | $Al_2O_3$ | 95.9 | 93.9 | 0.5 |
| 23 | 10% K | $Al_2O_3$ | 96.6 | 95.0 | 0 |
| 24 | 4.9 Cs | $Al_2O_3$ | 94.9 | 93.4 | 1.2 |
| 25 | 5% Mg | $Al_2O_3$ | 96.1 | 94.4 | 0 |

The catalyst was used in 0.5 g amount for 38.4 mmol of (all-rac)-α-tocopherol, the reactions were carried out at 100° C., reaction time was 15-24 hours,
(*)reaction time was 2.5-4 hours, the molar ratio α-tocopherol:acetic acid anhydride = 1:2.1;
*isolated in crude product;
**isolated after bulb-to-bulb distillation.

TABLE 2

Characterization of catalysts of Table 1

| Catalyst | Specific surface [$m^2/g$] | Volume of pores*) [ml/g] | Prepared from |
|---|---|---|---|
| 1 | n.d. | n.d. | $Ca(OH)_2$ + Na silicate |
| 2 | n.d. | n.d. | $Ca(OH)_2$ + Na silicate |
| 3 | 230 | 1.0 | $Ca(NO_3)_2$ |
| 4 | 230 | 1.0 | $Ca(NO_3)_2$ |
| 5 | 230 | 1.0 | $K_2CO_3$ |
| 6 | 230 | 1.0 | $Cs_2CO_3$ |
| 7 | 230 | 1.0 | $Cs_2CO_3$ |
| 8 | 230 | 1.0 | $K_2CO_3$ |
| 9 | 255 | 0.7 | $Ca(NO_3)_2$ |
| 10 | 75 | 0.6 | $Ca(NO_3)_2$ |
| 11 | 255 | 0.7 | $Ca(NO_3)_2$ |
| 12 | n.d. | 2.6 | $Ca(NO_3)_2$ |
| 13 | 270 | 1.0 | $Ca(NO_3)_2$ |
| 14 | 270 | 1.0 | $Ca(NO_3)_2$ |
| 15 | 255 | 0.7 | $Ba(NO_3)_2$ |
| 16 | 255 | 0.7 | $K_2CO_3$ |
| 17 | 255 | 0.7 | $(CH_3CO_2)_2Sr$ |
| 18 | 255 | 0.7 | $Ca(NO_3)_2$ + Na silicate |
| 19 | 255 | 0.7 | $Ca(NO_3)_2$ + Na silicate |
| 20 | ex Fluka | ex Fluka | KF |
| 21 | 252 | 1.0 | $K_2CO_3$ |
| 22 | 252 | 1.0 | $K_2CO_3$ |
| 23 | 252 | 1.0 | $K_2CO_3$ |
| 24 | 252 | 1.0 | $Cs_2CO_3$ |
| 25 | 252 | 1.0 | $Mg(NO3)_2$ |

*)determined by uptake of water at RT

EXAMPLE 4

Preparation of (all-rac)-α-tocopheryl acetate.

In a 50-ml four-necked flask equipped with a KPG-stirrer, thermometer, and a reflux condenser with an argon inlet, 16.8 g (38.4 mmol) of (all-rac)-α-tocopherol were dissolved in 8.23 g (80.6 mmol) of acetic anhydride in the presence of 0.5 g of a solid 22% Ca+26% Na on silicium oxide catalyst (No 2). The mixture was stirred at 400 rpm and heated at 100° C. (internal temperature) for 4 h. The mixture was cooled to 36° C., neutralized with 5 g $Na_2CO_3$, filtered, washed with 70 ml heptane and evaporated under reduced pressure (10 mbar, 40° C.). 18.57 g of a yellow oil were obtained representing (all-rac)-α-tocopheryl acetate with a purity of 94.46% (analyzed by GC, int. standard). Yield 96.7%, based on α-tocopherol. The crude product was further purified by bulb-to-bulb distillation at 209° C. (0.0071 mbar). The pure product was isolated as colorless-light yellowish oil in 96.27% purity (GC, int. standard). Yield 17.44 g (all-rac)-α-tocopheryl acetate; 96.1%, based on (all-rac)-α-tocopherol. In the distillation residue 0.1% of acetate was detected.

EXAMPLE 5

Preparation of (2R,4'R,8'R)-α-tocopheryl acetate.

In a 50-ml four-necked flask equipped with a KPG-stirrer, thermometer, and a reflux condenser with an argon inlet, 17.2 g (38.4 mmol) of (2R,4'R,8'R)-α-tocopherol were dissolved in 8.25 g (80.8 mmol) of acetic anhydride in the presence of 0.51 g of a solid 11% Ca+50% Na on silicium oxide catalyst (No 1). The mixture was stirred at 400 rpm and heated at 100° C. (internal temperature) for 3 h 30. The mixture was cooled to 30° C., neutralized with 5 g $Na_2CO_3$, filtered, washed with 70 ml heptane and evaporated under reduced pressure (10 mbar, 40° C.). 20.58 g of a yellow oil were obtained representing (2R,4'R,8'R)-α-tocopheryl acetate with a purity of 87.88%, (analyzed by GC, int. standard). Yield 99.7%, based on α-tocopherol. The crude product was further purified by bulb-to-bulb distillation at 201° C. (0.0071 mbar). The pure product was isolated as colorless-light yellowish oil in 92.49% purity (GC, int. standard). Yield 17.73 g (2R,4'R, 8'R)-α-tocopheryl acetate; 97.7%, based on α-tocopherol. In the distillation residue 0.3% of acetate was detected.

Based on chiral HPLC analysis, (2R,4'R,8'R)-α-tocopheryl acetate was obtained in 99.83% optical purity.

EXAMPLE 6

Preparation of (all-rac)-γ-tocopheryl acetate

In a 50-ml four-necked flask equipped with a KPG-stirrer, thermometer, and a reflux condenser with an argon inlet, 16.89 g (38.4 mmol) of (all-rac)-γ-tocopherol were dissolved in 8.23 g (80.6 mmol) of acetic anhydride in the presence of 0.51 g of a solid 11% Ca+50% Na on silicium oxide catalyst (No 1). The mixture was stirred at 400 rpm and heated at 100° C. (internal temperature) for 4 h 15. The mixture was cooled to 26° C., neutralized with 5 g $Na_2CO_3$, filtered, washed with 70 ml heptane and evaporated under reduced pressure (10 mbar, 40° C.). 19.15 g of a red oil were obtained representing (all-rac)-γ-tocopheryl acetate with a purity of 90.61% (analyzed by GC, int. standard). Yield 98.6%, based on γ-tocopherol. The crude product was further purified by bulb-to-bulb distillation at 200° C. (0.0076 mbar). The pure product was isolated as colorless-light yellowish oil in 92.68% purity (GC, int. standard). Yield 16.73 g (RRR)-γ-tocopheryl acetate; 95.0%, based on γ-tocopherol.

EXAMPLE 7

Preparation of (all-rac)-α-tocopheryl acetate

In a 50-ml four-necked flask equipped with a KPG-stirrer, thermometer, and a reflux condenser with an argon inlet, 17.04 g (38.4 mmol) (all-rac)-α-tocopherol were dissolved in 8.23 g (80.6 mmol) of acetic anhydride in the presence of 0.5 g KF on $Al_2O_3$ (No 20). The mixture was stirred at 400 rpm and heated at 100° C. (internal temperature) for 6 h. The mixture was cooled to 25° C., neutralized with 5 g $Na_2CO_3$, stirred for 15 minutes, filtered, washed with 70 ml heptane and evaporated under reduced pressure (10 mbar, 40° C.). 18.81 g of a yellowish oil was obtained representing, (all-rac)-α-tocopheryl acetate, with a purity of 95.91% analyzed by GC (int. standard). Yield 99.4%, based on (all-rac)-α-tocopherol. The crude product was further purified by bulb-to-bulb distillation at 200° C. (0.0092 mbar). The pure product was isolated as colorless-light yellowish oil in 95.93% purity (GC, int. standard). Yield 17.44 g (all-rac)-α-tocopheryl acetate, 96.1% based on (all-rac)-α-tocopherol. In the distillation residue 1.4% of (all-rac)-α-tocopheryl acetate were detected.

The invention claimed is:

1. A process for the manufacture of a tocopheryl acylate which comprises reacting a tocopherol with an acylating agent in the presence of a solid basic catalyst comprising an alkali metal and/or alkaline earth metal.

2. A process according to claim 1 wherein the basic alkali or alkaline earth metal catalyst comprises a solid carrier.

3. A process according to claim I wherein the acylating agent is an acid anhydride or an acyl halide.

4. A process according to claim 3 wherein the acyl group in the acylating agent is derived from an aliphatic carboxylic acid, preferably from a straight or branched chain $C_{1-7}$-alkanoic acid or a higher alkanoic acid with up to 20 carbon atoms, or from an aromatic carboxylic acid.

5. A process according to claim 4 wherein the acyl group in the acylating agent is derived from acetic acid, propionic acid, butyric acid, pivalic acid or benzoic acid.

6. A process according to claim 5 wherein the acylating agent is acetic anhydride or acetyl chloride.

7. A process according to claim 1 wherein the catalyst comprises an alkali metal on a solid support.

8. A process according to claim 1 wherein the catalyst comprises an alkaline earth metal on a solid support.

9. A process according to claim 1 wherein the catalyst comprises at least one alkali metal and at least one alkaline earth metal on a solid support.

10. A process according to claim I wherein the reaction is carried out with one of the reactants, the tocopherol or the acylating agent, in excess and in the absence of an added solvent.

11. A process according to claim 10 wherein the acylating agent is used in molar excess relative to the molar amount of tocopherol present in the initial reaction mixture.

12. A process according to claim 1, wherein (all-rac)-α-tocopherol or (RRR)-γ-tocopherol is acylated to (all_rac)-α-tocopheryl acetate or (RRR)-γ-tocopheryl acetate, respectively.

13. A process according to claim 7 wherein the alkali metal is Na or K on an $SiO_2$ or $Al_2O_3$ solid support.

14. A process according to claim 8 wherein the alkaline earth metal is Ca on an $SiO_2$ or $Al_2O_3$ solid support.

15. A process according to claim 11 wherein the acylating agent is used in a one-to about three-fold molar amount relative to the molar amount of tocopherol present in the initial reaction mixture.

16. A process according to claim 11 wherein the acylating agent is used in a 1.5 to 2.5-fold molar amount relative to the molar amount of tocopherol present in the initial reaction mixture.

17. A process according to claim 11 wherein the acylating agent is used in a 1.75 to 2.25-fold molar amount relative to the molar amount of tocopherol present in the initial reaction mixture.

* * * * *